United States Patent [19]

Kim

[11] Patent Number: 4,800,891
[45] Date of Patent: Jan. 31, 1989

[54] DOPPLER VELOCITY PROCESSING METHOD AND APPARATUS

[75] Inventor: Jin H. Kim, Pleasanton, Calif.

[73] Assignee: Siemens Medical Laboratories, Inc., Walnut Creek, Calif.

[21] Appl. No.: 120,573

[22] Filed: Nov. 13, 1987

[51] Int. Cl.$^4$ .............................................. A61B 10/00
[52] U.S. Cl. .............................. 128/661.09; 73/861.25
[58] Field of Search ................ 128/663; 364/415–416; 73/861.25

[56] References Cited

U.S. PATENT DOCUMENTS 4,391,148  7/1983  Sainz et al. ..................... 128/663 X
4,671,294  6/1987  Magnin et al. ...................... 128/663
4,697,594  10/1987  Mayo, Jr. ......................... 128/660 X

FOREIGN PATENT DOCUMENTS 0214654  3/1987  European Pat. Off. ....... 128/661.09

Primary Examiner—Francis Jaworski
Attorney, Agent, or Firm—Lawrence C. Edelman

[57] ABSTRACT

Method and apparatus for developing an estimation of the velocity of a moving target, comprising, transmitting groups of pulse signals towards the target, receiving groups of echo signals caused by reflections of the transmitted groups of pulse signals from the target and spatially processing the echo signals for developing the estimation of the velocity of the target. In a preferred embodiment, the spatial processing is for only a single pair of adjacent ones of ultrasonic echo signals and the estimation developes a two dimensional image of blood flow velocities in the body of a patient.

37 Claims, 4 Drawing Sheets

DOPPLER VELOCITY PROCESSING METHOD AND APPARATUS

BACKGROUND OF THE INVENTION

1. Field of the Invention

This invention relates to velocity estimation using Doppler techniques, and more particularly to a spatial vector averaging method and apparatus for estimating blood flow velocities in a medical diagnostic apparatus using ultrasonic pulse signals.

2. Background of the Invention

Medical diagnostic ultrasound apparatus generate images of anatomical structures within a body of a patient by transmitting ultrahigh-frequency sound waves (typically on the order of 3.0 MHz) into the patient and then analyzing the echoes, i.e., ultrasonic signals reflected from the structure of the body being scanned. Perhaps the most widely used ultrasound diagnostic apparatus displays in real-time anatomical information in the form of a two-dimensional image of a selected cross-section of the structure. The ultrasound signals are swept across the structure in the form of a sector scan. The sector scan is performed in real-time so that the image is available during the examination of the patient. In such cases, motion of the structure produces a corresponding moving image (i.e., a B-mode image).

In some clinical applications, e.g., cardiac imaging, anatomical defects can be relatively small and beyond the resolution capabilities of conventional anatomical ultrasound imaging. However, since a small anatomical defect may manifest itself by a pronounced change in blood flow velocity, for example aortic stenosis, mitral or aortic insufficiency or a congenital defect, a display of blood flow velocity would allow these abnormalities to be more easily detected. One known method for velocity display is to use FFT techniques to process the echo signals reflected from a selected small volume so as to generate a numerical display. This method is severely limited by the fact that velocity is only determined for the small sample volume and is also not a two dimensional real-time image. Real-time imaging of velocity in a larger area is highly desireable. Thus, velocity blood flow imaging has become an increasingly important portion of the ultrasound imaging device used in the medical diagnostic field, wherein a real-time blood flow image is superimposed over a real-time anatomical image. However, it is difficult to acquire sufficient ultrasound data to develop an accurate and high resolution blood flow image which can be displayed in real-time at a sufficiently high rate. This is because many echos need to be processed in a short time while the physical reality is that ultrasound signals have a relatively slow propagation speed in a human body, thereby limiting the number of echoes which can be received in a short time.

European Patent Publication No. 0 100 094 by Namekawa of the Aloka Company describes an ultrasound blood flow imaging apparatus for two-dimensional display i.e., mapping, of blood flow velocities within a body. The flow mapping is superimposed over a B-mode scan and displays blood flow in a color which is representative of the direction of the blood flow with respect to the ultrasonic transducer while variations in the intensity of the colors are representative of the blood flow velocities. It is only noted therein that the blood flow velocity signal is generated using a pulsed-Doppler method.

Present Dopper velocity estimators use time-domain processing techniques wherein a series of N repetitive pulses of RF-ultrasonic signal separated by time periods of T are transmitted towards a moving target along a given scan direction. A relatively large number of echo signals (from a minimum of 10 to a maximum of 256) are processed using Doppler techniques for determining the velocity and turbulence of the moving object. One such technique for determining Doppler frequency shift is shown, for example, by U.S. Pat. No. 4,542,657 issued to Barber et al. which uses I and Q sampled signals of a plurality (i.e., from 16 to 256) of the demodulated echo signals. FFT and zero-crossing velocity estimators are described in U.S. Pat. No. 4,318,413 for processing the Doppler signal. Another time-domain processing technique uses autocorrelaton (pulse-pair) algorithms, such as known, for example, from an article by Kasai et al. published in the IEEE Transactions on Sonics and Ultrasonics, Volume SU-32, No. 3, May 1985. Each of the above time-domain processing techniques evaluate a relatively large number of return echoes (from 10 to 256) for estimating blood flow velocity and turbulence.

For a better understanding of the time-domain processing technique and its relation to the present invention, reference is now made to FIG. 1a herein, which shows groups (or pulses) of ultrasonic signal 1, 2, 3, ... n which are excited and groups of return echo signals $e_1, e_2, e_3 ... e_n$ which are received in response thereto. The echoes are reflections from a target (i.e., blood) moving along a scan line A in a direction toward the ultrasonic transducer. FIG. 1b illustrates a rearrangement of six groups of the return echoes, wherein the t axis represents the axial depth or spatial direction and the tau axis represents the temporal direction. T represents the time delay, typically 200 microseconds, between the start of successive ultrasonic pulse transmissions. Note that the time shift between successive ones of the echoes is substantially uniform due to the relatively short time period between pulses as compared with the velocity of the moving target.

The autocorrelation method, which is generally recognized to provide superior performance for real-time blood flow imaging than the other known techniques, will be briefly described in conjunction with FIG. 1b. The autocorrelation type of time domain processing can be represented by the following equations:

For simplicity of formulations, we consider reflected echoes from a single target to be represented by $$Z(t) = a(t) \cos [w_0 t + \phi(t)] \qquad (1)$$

where a(t) is the ultrasonic signal pulse envelope, $w_0$ is the carrier frequency, and $\phi(t)$ is the phase response. When the target moves by a time shift $\alpha T$ during a pulse repetition period T, Eq. 1 for the n-th echo becomes $$Z_n(t) = a(t - \alpha nT) \cos [w_0(t - \alpha nT) + \phi(t - \alpha nT)] \qquad (2)$$

where $\alpha$ is the Doppler ratio given by $\alpha = w_d/w_0$ and $w_d$ is the Doppler frequency.

After quadrature demodulation, the demodulated signal $e_n(t)$ of Eq. (2) can be written as $$\begin{aligned} e_n(t) &= \tilde{a}(t - \alpha nT) e^{-j\alpha w_0 nT} \\ &= \tilde{a}(t - \alpha nT) e^{-j w_d nT} \end{aligned} \qquad (3)$$

-continued where $\tilde{a}(t) = \overline{a}(t)e^{j\phi(t)}$

In Eq. (3), $\tilde{a}(t)$ is mostly determined by the impulse response of the ultrasound transducer. For multiple targets having the same velocity, Eq. (3) is valid. However, the phase response of a(t) will include interference from multiple targets. If the multiple targets have different velocities, Eq. (3) will not be valid. However, we can approximate this situation by considering $\tilde{a}(t)$ as a broadband signal which has several frequency components. Consequently, our aim in flow imaging is to estimate the frequency mean and variance of the frequency spectrum of the demodulated signal given by Eq. (3).

In the known autocorrelation processing method, each echo signal vector $e_n$ is multiplied in the axial direction by the complex conjugate of the adjacent echo signal vector $e_{n-1}$, which results in a plurality of pulse-pair vector signals $e_1{}^*e_2, e_2{}^*e_3, e_3{}^*e_4, \ldots e_n e_{n-1}{}^*$. The amplitude of the resulting N-1 pulse-pair signals, at a certain axial depth represented by the Doppler time axis (the dashed line in FIG. 1b) are then averaged in the temporal (tau) direction.

The autocorrelation can be represented by two steps of pulse-pair vector calculation and averaging.

Pulse-pair vector calculation $$P(T; nT, t) = e_n(t)e_{n-1}{}^*(t) \quad (4)$$
$$= \tilde{a}(t - \alpha nT)\overline{a}[t - \alpha(n-1)T]e^{jw_dT}$$

Averaging $$R(T; nT, t) = \sum_{k=n}^{n+N-1} P(T; kT, t) \quad (5)$$
$$= \sum_{k=n}^{n+N-1} \tilde{a}(t - \alpha kT)\overline{a}[t - \alpha(k-1)T]e^{jw_dT}$$

where N is the number of temporal averagings. The phase of the pulse-pair vector in Eq. (4) represents instantaneous frequency of the input Doppler signal which is changing from pulse to pulse. The temporal averaging of Eq. (5) provides averaged vectors from which we can find a mean frequency.

From the amplitude and phase of the resultant averaged vectors, the mean frequency, which corresponds with the velocity of the blood, can be obtained. Furthermore, the variance (sigma squared) of the velocity can be obtained, which corresponds to the turbulence of the blood flow. Turbulence estimations also provide useful diagnostic information when displayed. The phase (velocity) and variance are calculated as follows:

$$\phi = \tan^{-1} \frac{R_i(T)}{R_r(T)} \quad (6)$$

$$\frac{2}{\sigma} = \frac{2}{T^2}\left[1 - \frac{|R(T)|}{R(0)}\right] \quad (7)$$

wherein R(T) is an abbreviated notation of R(T; nT, t) and $R(T) = R_r(T) + jR_i(T)$ For further details concerning this pulse-pair autocorrelation technique, the reader is referred to the forenoted article by Kasai et al.

Known autocorrelation velocity processing techniques suffer from the following two problems. Firstly, it is desirable that blood flow mapping have information updated on the order of 24–30 frames/second for best diagnostic effectiveness. Since existing autocorrelation techniques use temporal averaging, as exemplified by equations 1–7, averaging of a plurality (n) of received echo vectors is required. Thus, it is required to wait for the receipt of a plurality of echoes before an accurate analysis of the Doppler signal can be made. This results in a relatively low frame rate i.e., in the order of 15 frames/second. If less echoes were used the frame rate could be increased, however the accuracy of the velocity estimation would be severely degraded. Furthermore, since turbulence is in effect a differentiation of velocity with respect to time, due to amplitude fluctuations of the velocity signal, the receipt of even more echoes is required in order to arrive at an accurate turbulence estimation. The second problem results from the fact that the period of the amplitude and phase variations of the Doppler signal (the Doppler signal being the signal amplitude variations along a Doppler axis, such as shown in FIG. 1c) depends upon the blood flow velocity. In slower flows, the time shift between adjacent echoes is reduced. As can be easily visualized in FIG. 1a and 1b, this causes the period of the Doppler signal to become longer. Consequently, a greater number of echoes are required to be processed for accurate estimation of a slower velocity. In the known ultrasound systems employing velocity estimation, the number of received echoes which are averaged is decided by the maximum flow velocity (and is at least seven echo signals) so as to obtain accurate blood flow velocity mapping at about 15 frames/second. However, even more echo signals are required to be processed to develope an accurate blood flow map which includes slower velocities, thereby reducing the frame rate even more.

It is an object of the present invention to provide a Doppler blood flow velocity and turbulence estimator which minimizes the number of received echoes required for accurate estimation of blood flow velocity and turbulence in order that an accurate color blood flow mapping can be provided at a relatively high frame rate, for example 24 or 30 frames/second.

SUMMARY OF THE INVENTION

In accordance with the principles of the present invention, advantage is taken by the inventor of recognition of the fact that under some conditions, for example when a target (i.e., blood) is moving and the sampling point is at a fixed distance from the transducer (i.e., depth in the body), the result of conventional temporal averaging at that fixed depth is approximately the same as spatial averaging (i.e., averaging in the axial direction) of a single pulse-pair signal. Thus, in this case, estimation by temporal averaging of a plurality of pulse-pair signals is equivalent to estimation by spatial averaging of a single pulse-pair signal. Consequently, in accordance with the present invention, a single pair of echo signals are spatially averaged in order to develop a velocity estimation. In the preferred embodiment the spatial averaging of the echo signals is accomplished in the vector domain.

In accordance with a further aspect of the invention, since the processed pulse-pair signal has approximately twice the bandwidth of an individual echo signal, in order to ensure proper characterization of the echo signals for accurate digital processing, each individual echo signal is digitized in accordance with the Nyquist rate for the pulse-pair signal. That is, each echo signal is digitized so as to provide signal samples at approximately twice the Nyquist rate of the individual echo signals.

In accordance with a still further aspect of the invention the spatially averaged pulse-pair signal is also used to develop a turbulence estimation.

In accordance with an even further aspect of the invention the spatial vector averaging technique is combined with the temporal averaging technique under noisy signal conditions or when it is desired to make performance trade-offs between signal-to-noise and resolution. This results in improved performance for weak signals as compared with the use of spatial averaging only, yet results in improved speed of calculation if only temporal averaging were used.

Other features and advantages of the invention will be apparent from the following description of the preferred embodiments and from the claims.

For a fuller understanding of the present invention, reference should now be made to the following detailed description of the preferred embodiments of the invention and the accompanying drawings.

DETAILED DESCRIPTION OF THE PREFERRED EMBODIMENTS

Figure 1A:
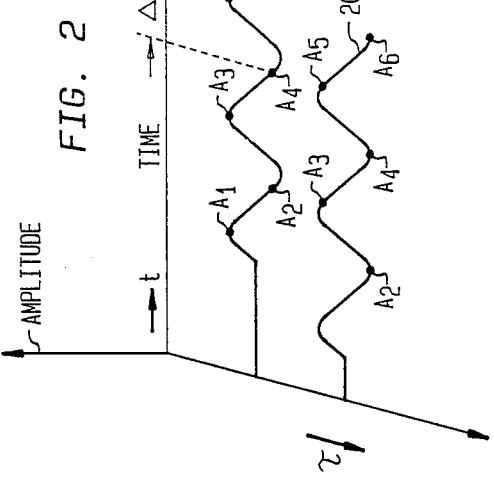
FIGS. 1a and 1b illustrate a series of pulse echos and a rearrangement of these echos, respectively, for illustrating the temporal averaging technique.
Figure 1B:
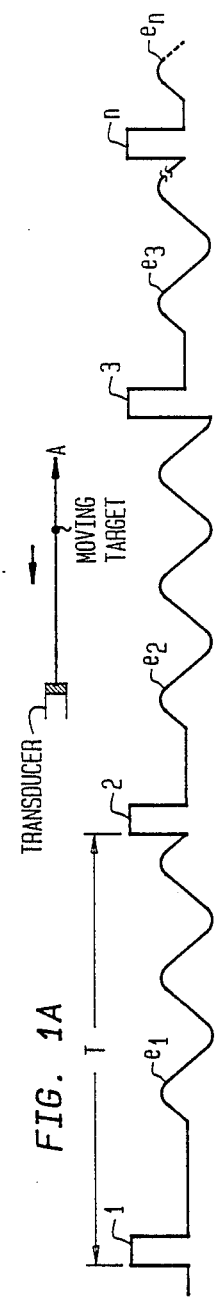
Figure 2:
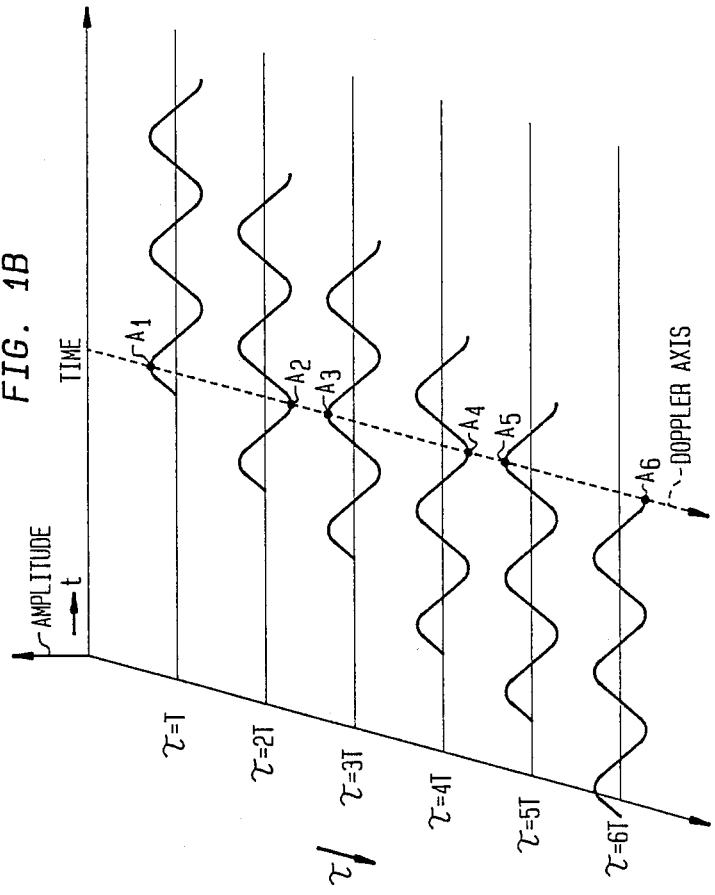
FIG. 2 illustrates two adjacent echo signals, which, when compared with FIG. 1(b) pictorially illustrates the approximate equivalence of the temporal and spatial averaging techniques.

FIG. 2, when viewed in conjunction with FIG. 1b, is useful for pictorially illustrating an equivalency between the temporal and spatial vector averaging techniques. As shown in FIG. 1b, the amplitude of the detected baseband signal of the return echoes is periodically sampled along the Doppler axis, generating amplitude samples $A_1, A_2 \ldots A_i$ (however, only $A_1$–$A_6$ are shown). Processing in accordance with temporal averaging techniques for velocity estimation, can be expressed in a digital form for equation (5) as follows:

$$R(T; nT, m) = \sum_{k=n}^{n+N-1} \tilde{a}(m\Delta - akT)\tilde{a}^*[m\Delta - a(k-1)T]e^{jwdT} \quad (8)$$

where $\Delta$ is the sampling interval in the spatial direction.

FIG. 2 shows only two of the sequentially received echoes. As visually illustrated therein, spatial sampling (in the t direction) results in paired amplitude samples $A_1 A_2, A_2 A_3, A_3 A_4 \ldots$ being generated which correspond with the same amplitude sample pairs $A_1 A_2, A_2 A_3, A_3 A_4 \ldots$ which were obtained by sampling along the Doppler axis in the temporal averaging technique. Spatial vector averaging (averaging along the t axis) of the amplitude sample pairs $A_1 A_2, A_2 A_3 \ldots$ of the single pulse-pair signal for velocity estimation can be expressed by $$R(T; nT, m) = \sum_{1=m}^{m+M-1} \tilde{a}(1\Delta - anT)\tilde{a}^*[1\Delta - a(n-1)T]e^{jwdT} \quad (9)$$

where M is the number of spatial averagings.

Note that in equation 8, the summation variable k modifies T, the time period between successive ones of the echo signals, while in equation 9, the summation variable 1 modifies $\Delta$, the time period between adjacent spatial samples. By comparing equations 8 and 9 and FIGS. 1b and 2 it is intuitively seen that with these given circumstances, temporal vector averaging of paired samples of a plurality of pulse-pair signals for obtaining a velocity estimation is approximately equivalent to spatial vector averaging of paired samples of a single pulse-pair signal for obtaining a velocity estimation. The equivalence is only approximate since in practice many times more paired samples can be spatially averaged as can be temporally averaged in a given time period (since only two echoes have to be received for this spatial averaging technique), thus resulting in a more accurate velocity estimation when using spatial vector averaging as compared with temporal averaging.

Figure 3:
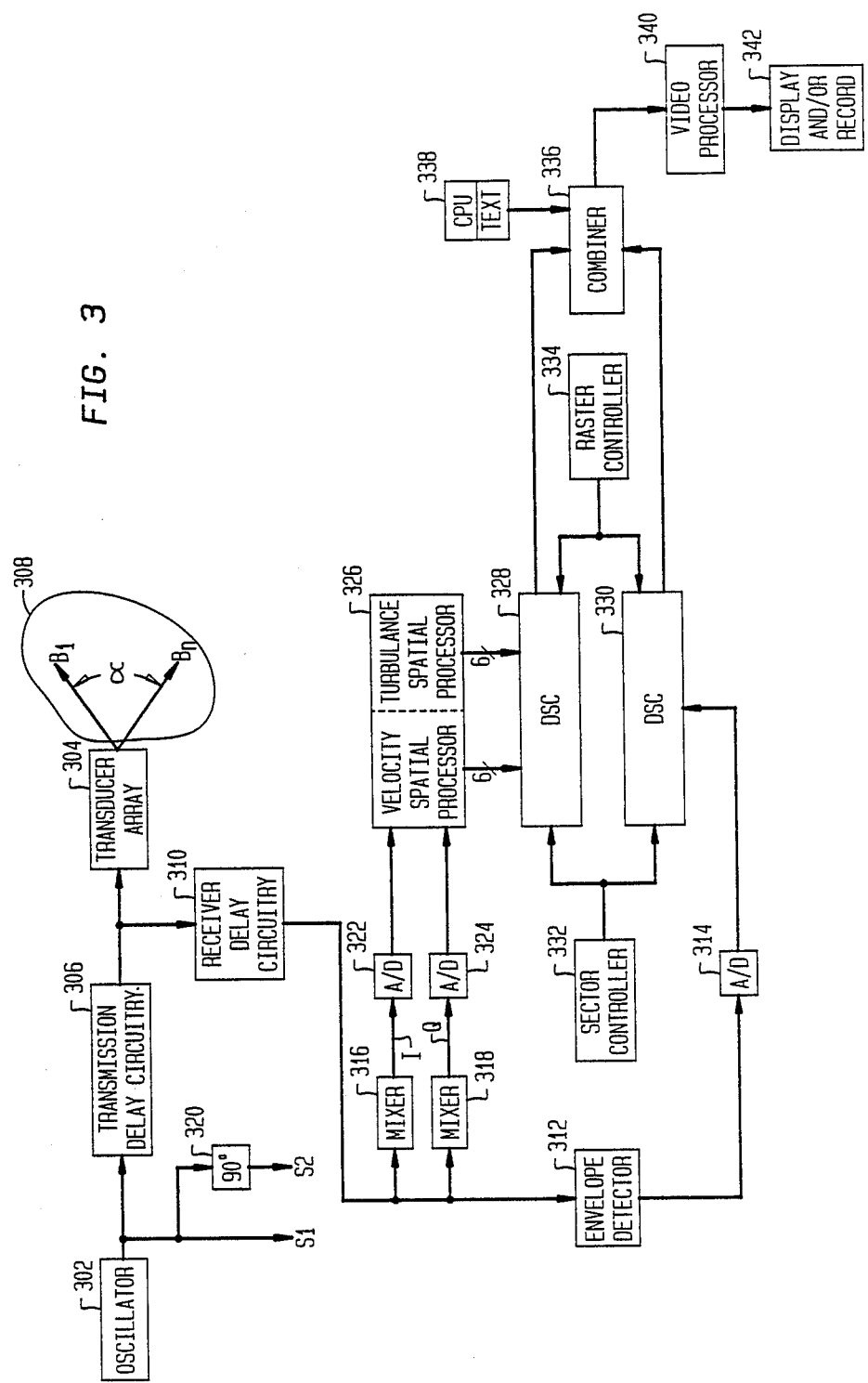
FIG. 3 illustrates, in block diagram form, an ultrasound imaging apparatus including pulse-pair spatial vector averaging in accordance with the principles of the present invention.

FIG. 3 illustrates a system block diagram of the inventive ultrasound medical imaging apparatus, and includes a reference oscillator 302 which provides a reference signal selected by the operator of the apparatus to be the operating frequency of an ultrasound transducer array 304. The reference signal is applied to controllable delay transmission circuitry 306, which includes a signal generator for developing a series of bursts of the reference signals, each series of bursts lasting no more than 8 microseconds and being repeated at 200 microseconds intervals. A plurality of controllable delay circuits, each having a digitally selectable delay, is responsive to each series of bursts for causing transducer array 304 to produce a series of beams of ultrasound $B_1$ through $B_n$ which are steered over an angle alpha so as to provide a standard sector scan image of the interior of an object 308, as well known.

Transducer array 304 is also connected to a receiver circuit 310 which includes a plurality of controllable delay circuits, each delay circuit having a digitally selectable delay for properly combining the echo signals received from the individual transducers of transducer array 304, in a conventional and well known manner. Additionally, as also conventionally known, controllable gain amplifiers for providing a time-gain compression characteristic are also provided in receiver circuitry 310. During the approximately 190 microsecond intervals between ultrasound transmissions, transducer array 304 serves as an ultrasound receiver and converts the reflected ultrasound signals (echoes) into electrical signals. The electrical signals are combined in accordance with the controllable delay circuitry, as well known, so that the signals provided by each transducer of the phase transducer array 304 are processed simultaneously as reflections from a central point.

The output signal of receiver circuitry 310 is applied to an envelope detector 312 which produces a positive output signal proportional to the amplitude of the signal provided from receiver circuitry 10. The amplitude signal provided from envelope detector 312 is then digitized by an analog-to-digital (A/D) converter 314. As will be subsequently described, this digitized echo signal is applied to a digital scan converter for converting the sector scan echo into a raster scan format for subsequent display and/or recording of the ultrasound generated image signals.

The output signal of receiver circuitry 310 is also coupled to the input of signal multipliers 316 and 318. Multipliers 316 and 318 comprise phase detectors having reference signal inputs S1 and S2, respectively. S1 is the reference signal provided from reference oscillator 302 and S2 is of the same frequency as S1 but has a phase which is shifted 90° with respect to the phase of S1 due to phase shifter circuit 320. As well known, with this arrangement multipliers 316 and 318 serve as in-phase and quadrature-phase synchronous detectors, and thereby provide in-phase (I) and quadrature-phase (Q) baseband vector components of the received echo signals. A/D converters 322 and 324 generate digitized versions of the I and Q signals, respectively.

A spatial vector processor 326 produces digital blood flow estimation signals which, over time are representative of a color blood flow image, and which are applied to a digital scan converter 328. Sptial vector processor 326 will be described in detail later on. As previously noted, the digitized echo signal is applied to digital scan converter 330. As is conventional in the art, a sector controller 332 controls the reading of the digital signals into digital scan converters 328 and 330 in accordance with the sector format and a raster controller 334 controls read-out of the digital signals from digital scan converters 328 and 330 in accordance with the raster format. A combiner 336 combines the digital signals from scan converters 328 and 330 so as to generate a signal representative of the anatomical image having superimposed thereover a color blood flow image representative of blood flow velocities. Combiner 336 has an additional input connected to the output of a central processing unit (CPU) 338 which, among other things, provides textual information including, for example, the name of a patient, medical history and operating instructions which may be selected from an operating menu for the ultrasound apparatus, in the conventional manner.

Combiner 336 provides red, green and blue output signals which are processed in a conventional manner by a video processor 340 and then applied to display and/or record devices 342. The display devices may comprise a color and a black and white CRT's and the record devices may comprise a strip recorder and a video tape recorder.

For further details concerning the structure and operation of FIG. 3, except for spatial processor 326, the reader is referred to U.S. Pat. No. 4,612,937 of Lawrence R. Miller, assigned to the same assignee as the present invention and which is incorporated herein by reference.

Figure 4:
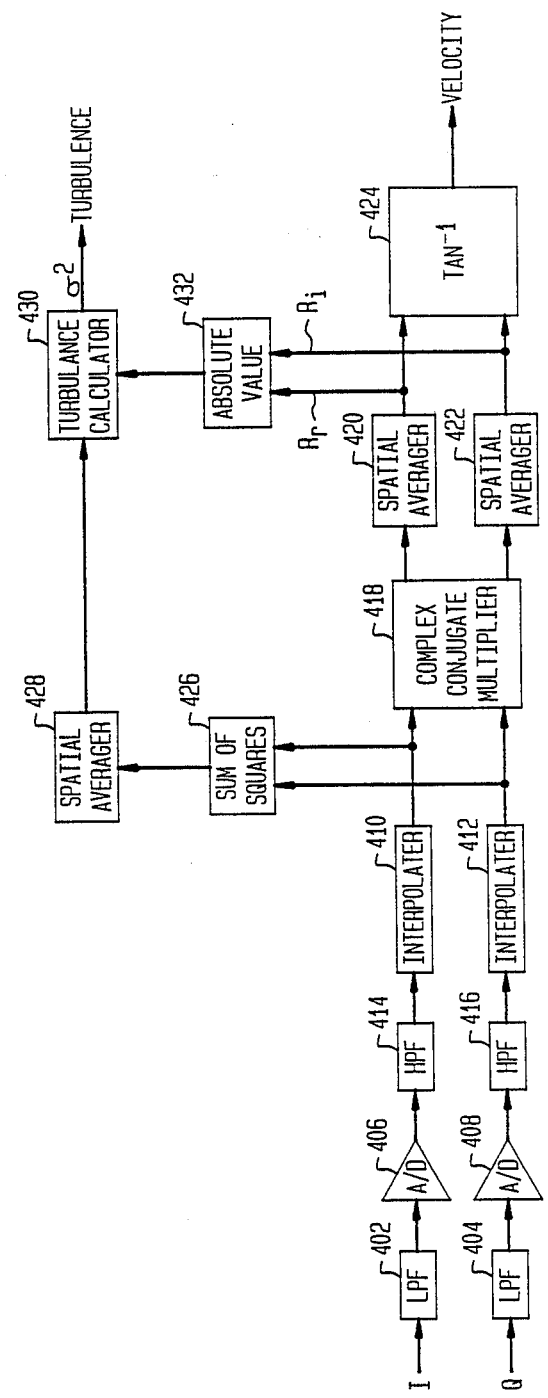
FIG. 4 illustrates, in functional block diagram form, the spatial vector averaging technique used in the velocity and turbulence estimation processing portion of the apparatus of FIG. 3.

Reference is now made to FIG. 4 which shows a functional block diagram of the spatial vector averager shown in FIG. 3. The demodulated I and Q vector signal components from quadrature multipliers 316 and 318 of FIG. 3 are applied to low pass filters (LPF) 402 and 404 for removing noise signals which are received with the incoming echo signals, as well as unwanted high frequency signal components supplied from multipliers 316 and 318. Next, A/D converters 406 and 408 digitize the I and Q components, respectively, in order that the remainder of the signal processing can be done in digital form. As previously noted, since spatial vector averaging uses significantly more information (bandwidth) of each received echo signal as compared with temporal processing, it is important that the digital characterization of each echo signal have enough samples so that the subsequent digital processing is accurate. Thus, each echo signal must provide signal samples to spatial processor 326 in accordance with the Nyquist rate of the pulse-pair signal which is processed therein. For example, if each echo signal has a bandwidth of 2.25 MHz, then echo signal samples must be provided to processor 326 at the 4.5 MHz rate. Ideally, A/D converters 406 and 408 would digitize the echo signals at this rate, however, it is presently more cost-effective to use slower speed, and hence lower cost A/D converter at 2.25 MHz and to use digital interpolators 410 and 412 (of conventional and well known construction) to arrive at the 4.5 MHz sample rate. Third order digital high pass filters (HPF's) 414 and 416 filter the I and Q signals, respectively, for the purpose of wall motion rejection, i.e., for rejection of wall motions which are relatively slow as compared with the blood flow velocity. The cut-off frequency of HPF's 414 and 416 are also adjustable, for example, from 66 Hz to 526 Hz when using a 5 MHz sampling rate for the transmitted ultrasound signals in order to properly reject varying amounts of wall motion. HPF's 414 and 416 are conventionally implemented as digital delay line cancellers (DLC) and are well known to those skilled in the art.

As in the case with the temporal type of velocity processing, spatial averaging velocity processing includes a covariance algorithm wherein:

(1) Pulse-pair vectors are calculated by complex conjugate multiplication of successive echoes, (2) The real and imaginary parts of the resultant vectors are averaged, and (3) The mean frequency (velocity) of the blood flow is determined by calculating the phase of the averaged vectors.

Thus, a complex conjugate multiplier 418 receives the I and Q echo signal components and calculates pulse-pair vector components using successive echo signals by complex conjugate multiplications in accordance with equation (4).

Next, the real and imaginary parts of the pulse-pair vectors are spatially averaged over their coherence interval (pulse width) by spatial averagers 420 and 422, respectively. The mean frequency (velocity) is determined by computing the phase of the echo vector using a $\tan^{-1}$ circuit 424. That is, by calculating the $\tan^{-1}$ of the ratio of imaginary and real portions of the pulse-pair vector, a velocity estimation is produced.

A turbulence estimation is also produced. As shown in equation 7, the turbulence estimation is proportional to the ratio of the absolute value of R(T) and R(0). R(0) corresponds to the power of the received echo signal, and is calculated by summing the squares of the I and Q echo signal components. This is accomplished by squaring circuit 426. For accuracy, the calculated power is spatially averaged by averager 428 to the same degree of spatial averaging provided by averagers 420 and 422, and applied to one input of a turbulence estimation calculator 430. An absolute value circuit 432 provides the absolute value of R(T) to another input of turbulence estimation calculator 430. The turbulence estimation is provided at the output of calculator 430.

Figures 5, 6:
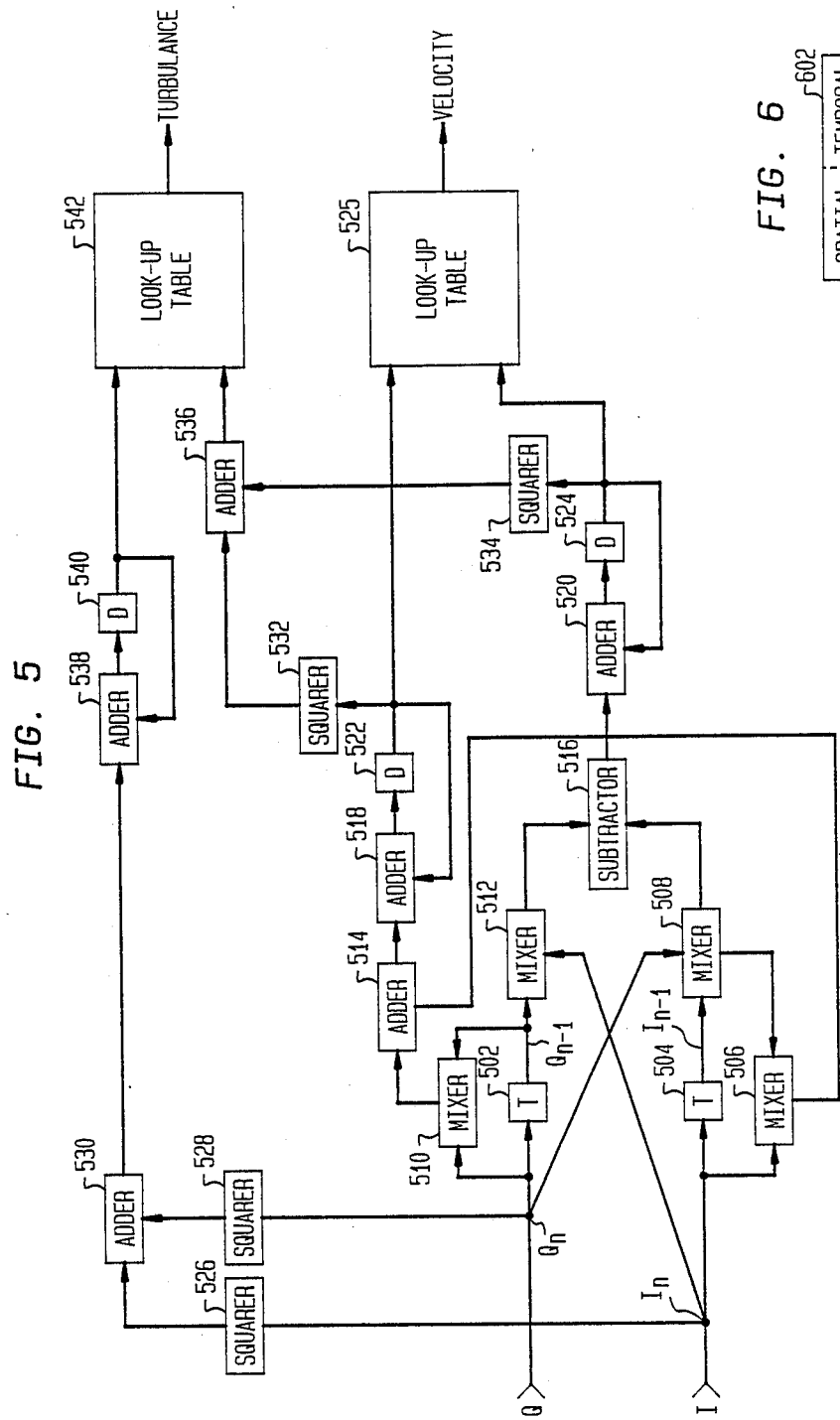
FIG. 5 illustrates, in block diagram form, a hardware implementation of the functional block diagram of FIG. 4.
FIG. 6 illustrates, in functional block diagram form, a modified version of the spatial vector averager of FIG. 4 which is particularly useful for weak signals.

FIG. 5 illustrates in block diagram form a hardware implementation for the FIG. 4 arrangement. Complex conjugate multiplication of the echo vector signals is accomplished as shown below:

$$e_n = I_n + jQ_n$$

$$e_{n-1} = I_{n-1} + jQ_{n-1}$$

$$e_n e_{n-1}^* = R_i + jR_j$$

wherein $$R_i = I_n I_{n-1} + Q_n Q_{n-1}$$

and $$R_j = I_n Q_{n-1} - I_{n-1} Q_n$$

Thus, with the delay provided by delay circuits 502 and 504 equal to the time delay T between successive echo signals, the output of mixer 506 is $I_n I_{n-1}$, mixer 508 is $I_{n-1} Q_n$, mixer 510 is $Q_n Q_{n-1}$ and mixer 512 is $I_n Q_{n-1}$. Thus, the output of adder 514 is $R_i$ and the output of adder 516 is $R_j$. Adders 518 and 520 provide recursive additions of the $R_i$ and $R_j$ vector components, respectively, each addition providing a spatial averaging of the respective vector components due to time delay circuits 522 and 524 coupled in a feedback manner to adders 518 and 520, respectively. The delay ($\Delta$) provided by time delay circuits 522 and 524 is significantly shorter than the delay provided by circuits 502 and 504 so as to effectuate spatial averaging, i.e., the delays correspond with the time periods between successive samples $A_1, A_2, A_3 \ldots A_i$ of each echo signal of FIG. 2. The number of spatial averagings is set by periodically resetting the output of averagers 420 and 422 to zero after e.g., 5-20 successive spatial averagings of the pulse-pair signal samples. It is noted that although averaging beyond the coherence interval increases the signal-to-noise of the estimation, it reduces its resolution. The $\tan^{-1}$ calculation is provided by a look-up table (memory) 525 which receives the spatially averaged digital $R_i$ and $R_j$ signals as an address and is programmed to provide as its output the $\tan^{-1}$ of $R_j/R_i$, which is representative of the mean velocity of the blood flow in a selected sample volume of the ultrasound sector scan.

For turbulence estimation, circuits 426 and 432 comprise squaring circuits 526, 528 and adder 530, and squaring circuits 532, 534 and adder 536, respectively. The turbulence calculation is provided by a look-up table 538 which receives the processed digital R(0) and R(T) signals as an address and is programmed to provide as its output a signal corresponding to $$\left[1 - \frac{|R(T)|}{R(O)}\right],$$

which is proportional to the turbulence estimation for the blood flow in the selected sample volume of the ultrasound sector scan. Note that in theory, a square root circuit should be provided after adder 536, however, in practice the effect of the square root circuit can be pre-programmed into look-up table 538, thereby eliminating the need for a square root circuit.

It is noted that good turbulence estimation generally requires averaging of ten or more echoes. Thus, the above-described spatial vector averaging which uses only a single pulse-pair (i.e., two echoes) will provide a lower resolution turbulence estimation than conventional temporal averaging. Furthermore, it is known that for weak Doppler signals, more averagings are generally required for accurate estimations. Therefore, in accordance with a further aspect of the present invention, the previously described spatial averaging technique can be modified so as to include temporal signal processing in conjunction with spatial averaging, when desired. This type of processing is referred to herein as two-dimensional vector averaging because the echo vector signals are processed and averaged in a matrix of two dimensions, one axis of the matrix is the axial (spatial) direction and an orthogonal axis is the t (temporal) direction. In this case, spatial averagers 420 and 422 of FIG. 4 would each be replaced by a spatial/temporal averager 602, such as shown in FIG. 6. Averager 602 comprises a spatial averager such as illustrated in FIGS. 4 and 5, followed by a temporal averager of conventional design. The temporal averager would temporally process corresponding signal samples from pairs of successive echo signals, for example 4 pairs (using 5 sequential echo signals), so as to generate in combination with, for example, 5 spatial averagings for each pulse-pair, 20 averagings. This results in improved resolution turbulence estimations as compared with the use of spatial averagings only, and improved resolution velocity estimations as compared with the use of spatial averaging only during the reception of weak signals. Of course, performance trade-offs are also possible, e.g., for a higher frame-rate mode, 20 spatial averagings only could be used, i.e., no temporal averagings.

Thus, there has been shown and described novel apparatus for processing ultrasound echo signals for developing blood flow estimation signals which fulfull all the objects and advantages sought therefore. Many changes, modifications, variations and other uses and applications of the subject invention will, however, become apparent to those skilled in the art after considering this specification and the accompanying drawings which disclose only preferred embodiments thereof. For example, the described spatial processing estimation techniques could be applied in fields other than ultrasound, for example, in radar or other types of Doppler systems. Additionally, portions of the signal processing shown as being implemented in hardware in FIG. 5, could be implemented in software. All such changes, modifications, variations and other uses and applications which do not depart from the spirit and scope of the invention are deemed to be covered by the invention as defined only by the claims which follow.

I claim:

1. A method for developing an estimation of the velocity of a moving target, comprising:
   transmitting groups of pulse signals towards said target;
   receiving groups of echo signals caused by reflections of said transmitted groups of pulse signals from said target;
   converting said received echo signals into real and imaginary vector signal components;
   vector processing of two temporally successive groups of said echo signals in their vector component format so as to develop real and imaginary processed vector signal components;

spatial averaging of said real and imaginary processed vector components; and calculating said velocity estimation from said spatially averaged real and imaginary processed vector signal components.

2. The method of claim 1, wherein said vector processing step comprises:

vector processing of only a single pair of temporally successive groups of said echo signals for use in developing said estimation of the velocity of said target.

3. The method of claim 1, wherein said vector processing and spatial averaging steps comprise:

correlation processing of said two temporally successive groups of echo signals.

4. The method of claim 3, wherein said correlation processing step comprises:

complex conjugate multiplication of said two temporally successive groups of echo signals.

5. The method of claim 3, wherein said calculating step comprises:

calculating the arctan of a ratio of the spatially averaged imaginary and real processed vector components for developing a signal representative of said velocity estimation.

6. The method of claim 1, wherein said calculating step comprises:

calculating the arctan of a ratio of the spatially averaged imaginary and real processed vector components for developing a signal representative of said velocity estimation.

7. The method of claim 1, further comprising:

digitizing said groups of echo signals before said vector processing step, said digitizing resulting in echo signals samples being generated at a rate of approximately twice the Nyquist rate for each of said groups of echo signals.

8. The method of claim 1 wherein said spatial averaging step comprises:

spatial averaging of a plurality of pairs of temporally successive ones of said echo signals in combination with temporal averaging of the results of said spatial averaging for each of said plurality of pairs of temporally successive echo signals for developing said velocity estimation.

9. The method of claim 8, comprising the further step of:

calculating a turbulence estimation using said spatially and temporally averaged echo signals.

10. The method of claim 1, including the further steps of:

repeatedly calculating velocity estimations in accordance with said prior steps so as to develop a two dimensional array of said velocity estimations over a given scan area; and displaying said two dimensional array of velocity estimations so as to develope an image of velocity estimations within said given scan area.

11. A method according to claim 1, comprising the further step of:

calculating a turbulence estimation using said spatially averaged processed vector components.

12. A method for developing an estimation of the velocity of a moving target, comprising:

transmitting groups of signals toward said target;

receiving groups of echo signals caused by reflections of said transmitted groups of pulse signals from said target; and digital autocorrelation processing with spatial averaging of said echo signals for developing said estimation of the velocity of said moving target, wherein a digitizing step precedes said autocorrelation processing and spatial averaging step and generates digitized samples of said echo signals at a minimum rate of approximately twice the Nyquist rate for an individual one of said echo signals.

13. The method according to claim 12 wherein said autocorrelation processing with spatial averaging step comprises:

complex conjugate multiplication of two adjacent groups of said echo signals for developing vector component signals and spatial averaging of said vector component signals.

14. The method according to claim 13 further including:

calculating the arctan of the ratio of the spatially averaged vector components for developing a signal representative of said velocity estimation.

15. The method according to claim 14 further including:

calculating a turbulence estimation using said spatially averaged vector components.

16. The method of claim 12, including the further steps of:

repeatedly calculating velocity estimations in accordance with said prior steps so as to develop a two dimensional array of said velocity estimations over a given scan area; and displaying said two dimensional array of velocity estimations so as to develop an image of velocity estimations within said given scan area.

17. A method for developing an estimation of the velocity of a moving target, comprising:

transmitting groups of pulse signals towards said target;

receiving groups of echo signals caused by reflections of said transmitted groups of pulse signals from said target;

complex conjugate multiplication of a pair of temporally successive groups of said echo signals for developing vector component signals;

spatial averaging of said vector component signals; and repetition of said above two steps for a successive pair of temporally successive groups of received echo signals for developing said estimation of the velocity of said target.

18. The method of claim 17, including the further steps of:

repeatedly calculating velocity estimations in accordance with said prior steps so as to develop a two dimensional array of said velocity estimations over a given scan area; and displaying said two dimensional array of velocity estimations so as to develop an image of velocity estimations within said given scan area.

19. Apparatus for developing an estimation of the velocity of a target, comprising:

means for transmitting groups of pulse signals towards said target;

means for receiving groups of echo signals caused by reflections of said transmitted groups of pulse signals from said target;

spatial averaging means for spatially averaging said echo signals for developing said estimation of the velocity of said target, said spatial averaging means including delay means having a time delay equal to the time delay between adjacent groups of said transmitted pulse signals; and an adder having said delay means coupled thereto in a feedback manner so as to repeatedly perform spatial averagings of at least one pair of temporally successive ones of said echo signals.

20. Apparatus according to claim 19 further including:

means for calculating a turbulence estimation from said spatially averaged echo signals.

21. The apparatus of claim 19, wherein:

said spatial averaging means averages only a single pair of temporally successive ones of said echo signals for developing said estimation of the velocity of said target.

22. The apparatus of claim 19, wherein said spatial averaging means includes:

means for converting said received echo signals into real and imaginary vector signal components;

means for vector processing of two temporally successive groups of said echo signals in their vector component format so as to develop real and imaginary processed vector signal components;

means for spatial averaging of said real and imaginary processed vector components; and means for calculating said velocity estimation from said spatially averaged real and imaginary processed vector signal components.

23. The apparatus of claim 22, wherein said vector processing means comprises:

means for correlation processing of said two temporally successive groups of said echo signals.

24. The apparatus of claim 23, wherein said correlation processing means comprises:

a complex conjugate multiplier for multiplying said two temporally successive groups of echo signals together in a complex conjugate manner.

25. The apparatus of claim 24, wherein said calculating means comprises:

means for calculating the arctan of a ratio of the spatially averaged imaginary and real processed vector components for developing a signal representative of said velocity estimation.

26. The apparatus of claim 25, wherein said means for calculating the arctan comprises:

a look-up table memory which is addressed by said spatially averaged imaginary and real vector components.

27. The apparatus of claim 19, further including:

means for digitizing said groups of echo signals so as to supply to said spatial averaging means echo signal samples at a rate of approximately twice the Nyquist rate for each of said groups of echo signals.

28. Apparatus according to claim 19, further including:

means for temporally averaging the results of said spatial averaging means, for developing said estimation of the velocity of said target.

29. Apparatus for developing an estimation of the velocity of a moving target, comprising:

means for transmitting groups of signals toward said target;

means for receiving groups of echo signals caused by reflections of said transmitted groups of pulse signals from said target;

means for digitizing said echo signals; and means for digital autocorrelation processing with spatial averaging of said digitized echo signals for developing said estimation of the velocity of said moving target, wherein said digitizing means generates digitized samples of said echo signals at a minimum rate of approximately twice the Nyquist rate for an individual one of said echo signals.

30. Apparatus according to claim 29 wherein said means for autocorrelation processing with spatial averaging comprises:

a complex conjugate multiplier for multiplying said two adjacent groups of said echo signals together in a complex conjugate manner for developing vector component signals and spatial averaging of said vector component signals.

31. Apparatus according to claim 30 further including:

means for calculating the arctan of a ratio of the spatially averaged vector components for developing a signal representative of said velocity estimation.

32. Apparatus according to claim 31 further including:

means for calculating a turbulence estimation using said spatially averaged vector components.

33. Apparatus according to claim 29, further including:

means for repeatedly calculating velocity estimations so as to develope a two dimensional array of said velocity estimations over a given scan area; and means for displaying said two dimensional array of velocity estimations so as to develope an image of velocity estimations within said given scan area.

34. Apparatus according to claim 29, further including:

means for temporally averaging the results of said spatial averaging means, for developing an estimation of the turbulence of said target.

35. Apparatus for developing an estimation of the velocity of a moving target, comprising:

means for transmitting groups of pulse signals towards said target;

means for receiving groups of echo signals caused by reflections of said transmitted groups of pulse signals from said target;

means for complex conjugate multiplication of a pair of temporally successive groups of said echo signals for developing vector component signals;

means for spatial averaging of said vector component signals; and means for temporal averaging of the results of said spatial averagings for a successive pair of temporally successive groups of said echo signal for developing said estimation of the velocity of said target.

36. Apparatus according to claim 35 further including:

means for calculating a turbulence estimation from said spatially and temporally averaged vector components.

37. Apparatus according to claim 35, further including:

means for repeatedly calculating velocity estimations so as to develope a two dimensional array of said velocity estimations over a given scan area; and means for displaying said two dimensional array of velocity estimations so as to develope an image of velocity estimations within said given scan area.

* * * * *